(12) United States Patent
Mace et al.

(10) Patent No.: US 9,410,953 B2
(45) Date of Patent: Aug. 9, 2016

(54) USE OF NON-NUCLEOPHILIC ADDITIVES FOR REDUCTION OF SURFACE MORPHOLOGICAL ANOMALIES IN PROBE ARRAYS

(75) Inventors: Charles R. Mace, Auburn, NY (US); Amrita R. Yadav, Rochester, NY (US); Benjamin L. Miller, Penfield, NY (US)

(73) Assignee: University of Rochester, Rochester, NY (US)

( * ) Notice: Subject to any disclaimer, the term of this patent is extended or adjusted under 35 U.S.C. 154(b) by 357 days.

(21) Appl. No.: 13/122,228

(22) PCT Filed: Sep. 30, 2009

(86) PCT No.: PCT/US2009/058991
§ 371 (c)(1),
(2), (4) Date: Jul. 20, 2011

(87) PCT Pub. No.: WO2010/039808
PCT Pub. Date: Apr. 8, 2010

(65) Prior Publication Data
US 2011/0275532 A1 Nov. 10, 2011

Related U.S. Application Data

(60) Provisional application No. 61/101,831, filed on Oct. 1, 2008.

(51) Int. Cl.
| | | |
|---|---|---|
| C40B 50/14 | (2006.01) | |
| C40B 30/04 | (2006.01) | |
| C40B 40/06 | (2006.01) | |
| G01N 33/543 | (2006.01) | |
| B01J 19/00 | (2006.01) | |
| C12Q 1/68 | (2006.01) | |

(52) U.S. Cl.
CPC ....... *G01N 33/54393* (2013.01); *B01J 19/0046* (2013.01); *C12Q 1/6837* (2013.01); *G01N 33/54353* (2013.01); *B01J 2219/0074* (2013.01); *B01J 2219/00533* (2013.01); *B01J 2219/00612* (2013.01); *B01J 2219/00626* (2013.01); *B01J 2219/00637* (2013.01); *B01J 2219/00659* (2013.01); *B01J 2219/00725* (2013.01)

(58) Field of Classification Search
CPC .............................. B01J 2219/00533
USPC ........................................................ 506/9
See application file for complete search history.

(56) References Cited

U.S. PATENT DOCUMENTS

| | | | | |
|---|---|---|---|---|
| 6,197,274 | B1 * | 3/2001 | Mahmud et al. | 423/449.2 |
| 2003/0032203 | A1 * | 2/2003 | Sabatini et al. | 436/518 |
| 2003/0203205 | A1 * | 10/2003 | Bi et al. | 428/402 |
| 2004/0110276 | A1 * | 6/2004 | Amontov et al. | 435/287.2 |
| 2005/0153429 | A1 | 7/2005 | Liebmann-Vinson et al. | |
| 2008/0085060 | A1 * | 4/2008 | Bosco et al. | 382/264 |
| 2008/0179571 | A1 | 7/2008 | Sen et al. | |
| 2008/0213910 | A1 * | 9/2008 | Jogikalmath | 436/86 |
| 2011/0318226 | A1 * | 12/2011 | Ge et al. | 422/63 |

FOREIGN PATENT DOCUMENTS

WO 2004/056402 A2 7/2004

OTHER PUBLICATIONS

MacBeath et al., Printing Proteins as Microarrays for High-Throughput Function Determination, Science, Sep. 8, 2000, vol. 289, pp. 1760-1763.*
M. Lee et al Protein nanoarray on Prolinder surface constructed by atomic force microscopy dip pen nanolithography for analysis of protein interactions, Proteomics, Jan. 3, 2006, 6, pp. 1094-1103.*
Y. Lee et al Proteochip: a highly sensitive protein microarray prepared by a novel method of protein immobilization for applications of protein-protein interaction studies, Dec. 2003, 3(12), pp. 2289-2304.*
Ling et al., Multiplexing molecular diagnostics and immunoassays using emerging microarray technologies, Expert Reviews Molecular Diagnostics, Jan. 2007, (7)1, pp. 87-98.*
Tjernberg et al., J Biomol. Screen, 2006, 11, pp. 131-137.*
Vandevelde et al., Langmuir, 2007, 23, pp. 6390-6493.*
Bouaidat et al., Lab Chip, 2004, 4 pp. 632-637.*
Gutmann et al., Lab Chip, 2005, 5, pp. 675-681.*
Gosalia et al., PNAS, Jul. 22, 2003, 100(15), pp. 8721-8726.*
Baca et al., Fabricating Protein Arrays, Proteins and Proteomics, Cold Spring Harbor Press, Chapter 10, 2007, pp. 669-697.*
Kim et al. (NSTI Nanotech 2006 Conference and Trade Show, May 6-11, 2006, Optimizing antibody microarrays for high resolution SPR microscopy, pp. 1-4).*
Bibliographic information for Kim et al.*
Belmont et al.(Applied Physics Letters, May 7, 2007, 90, pp. 193101-1 to 193101-3.*
Uttamchandani et al., Current Opinion in Chemical Biology, 2005, 9: pp. 4-13.*

(Continued)

*Primary Examiner* — Larry Riggs
*Assistant Examiner* — Karla Dines
(74) *Attorney, Agent, or Firm* — LeClairRyan, a Professional Corporation

(57) ABSTRACT

The present invention relates to a formulations and methods for coupling a reactant (or probe precursor) to a functionalized surface for purposes of forming an arrayed sensor. This method includes the steps of: providing a surface having a reactive functional group; and introducing onto the surface, at a plurality of discrete locations, two or more compositions of the invention, which include a different reactant (probe precursor) and a non-nucleophilic additive, wherein such introduction is carried out under conditions effective to allow for covalent binding of the reactant to the surface via the reactive functional group. This results in a probe-functionalized array that substantially overcomes the problem of surface morphological anomalies on the array surface. Use of the resulting arrays in various detection systems is also encompassed.

21 Claims, 5 Drawing Sheets

(56) References Cited

OTHER PUBLICATIONS

ISA220 International Search Report and Written Opinion for PCT/US09/58991, Dec. 4, 2009.
Deng et al., J. Am. Chem. Soc. 128:2768-2769 (2006).
Deegan et al., Nature 389:827-829 (1997).
Gutmann et al., "Non-Contact Production of Oligonucleotide Microarrays Using the Highly Integrated TopSpot Nanoliter Dispenser," Analyst 129:835-840 (2004).
Preininger et al., "Optimizing Processing Parameters for Signal Enhancement of Oligonucleotide and Protein Arrays on ARChip Epoxy," Bioelectrochem. 67:155-162 (2005).
Koops et al., "Effect of Chemical Modification on the Activity of Lipases in Organic Solvents," Enzyme Microbial Technol. 25:622-631 (1999).
Fung et al., "Analysis of Leachable and Total Trace Metals in Air Particulate matters by Capillary Electrophoresis," Talanta 45:619-629 (1998).
Mace et al., "Investigation of Non-Nucleophilic Additives for the Reduction of Morphological Anomalies in Protein Arrays," Langmuir 24:12754-12757 (2008).
Supplementary European Search Report for EP Patent Application No. 09818429, dated Mar. 29, 2012.

\* cited by examiner

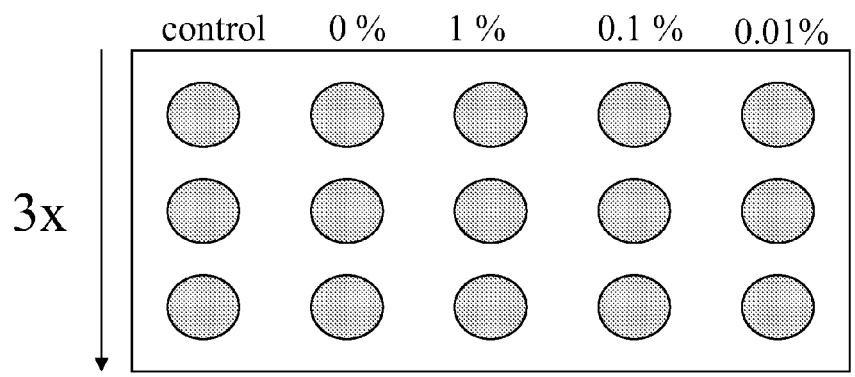
Figure 4
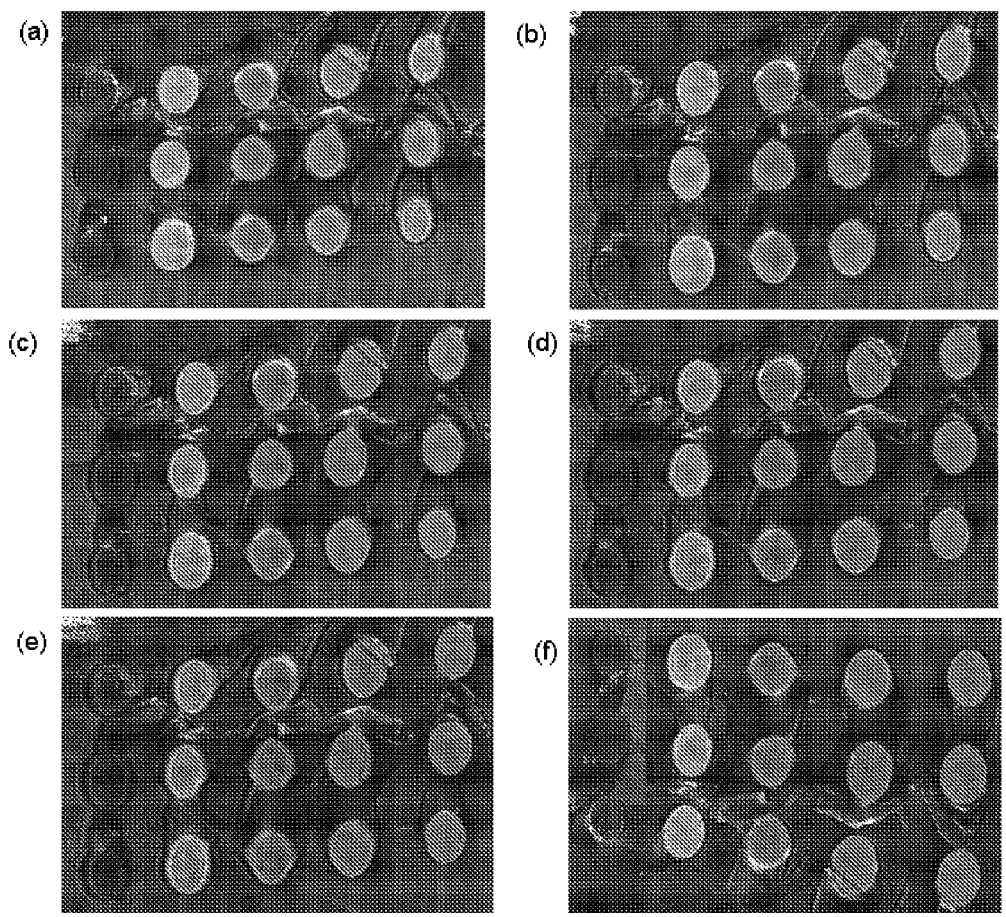
Figures 5A-F

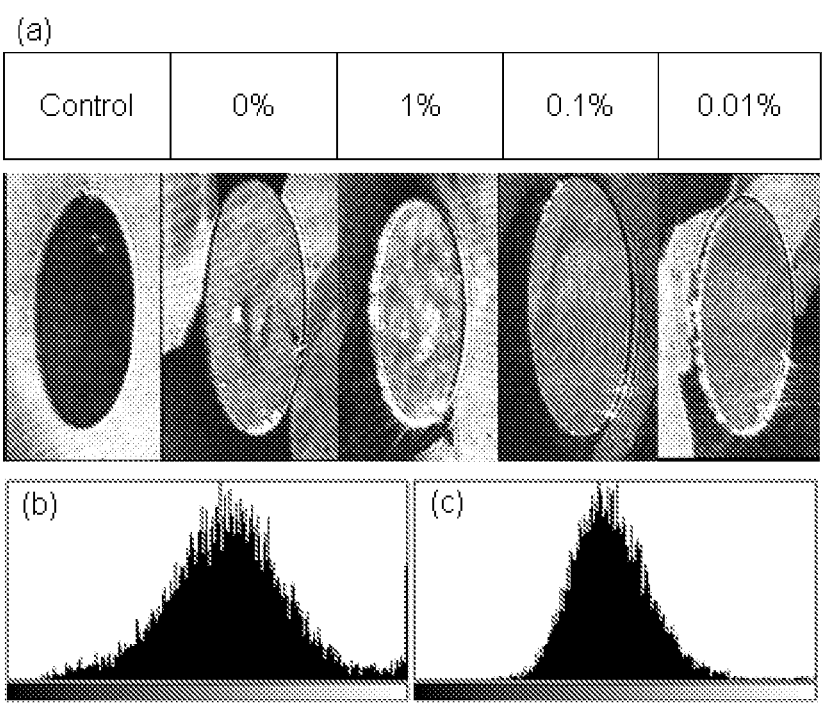
Figures 6A-C

USE OF NON-NUCLEOPHILIC ADDITIVES FOR REDUCTION OF SURFACE MORPHOLOGICAL ANOMALIES IN PROBE ARRAYS

This application is a national stage application under 35 U.S.C. 371 from PCT Application No. PCT/US09/58991, filed Sep. 30, 2009, which claims benefit of U.S. Provisional Patent Application Ser. No. 61/101,831, filed Oct. 1, 2008, which is hereby incorporated by reference in its entirety.

This invention was made with government support under grant R24-AL054953 and UL1-RR024160 awarded by the National Institutes of Health. The government has certain rights in the invention.

FIELD OF THE INVENTION

The present invention relates to methods and formulations for the preparation of arrayed detection devices, and particularly the resulting arrayed chips, which can be used in various detection systems.

BACKGROUND OF THE INVENTION

A variety of attachment chemistries have been developed for the covalent immobilization of probe molecules in DNA or protein arrays (Guo et al., "Direct Fluorescence Analysis of Genetic Polymorphisms by Hybridization with Oligonucleotide Arrays on Glass Supports," *Nucleic Acid Res.* 22:5456-5465 (1994); Tomizaki et al., "Protein-Detecting. Microarrays Current," *Chem. Bio. Chem.* 6:782-799 (2005); MacBeath et al., "Printing Proteins as Microarrays for High-Throughput Function Determination," *Science* 289:1760-1763 (2000); Li et al., "Adapting cDNA Microarray Format to Cytokine Detection Protein Arrays," *Langmuir* 19:1557-1566 (2003), which are hereby incorporated by reference in their entirety). With few exceptions, for example, thiol-mediated attachment to gold (Bain et al., "Formation of Monolayer Films by the Spontaneous Assembly of Organic Thiols from Solution onto Gold," *J. Am. Chem. Soc.* 111:321-335 (1989); Nuzzo et al., "Fundamental Studies of Microscopic Wetting on Organic Surfaces. 1. Formation and Structural Characterization of a Self-Consistent Series of Polyfunctional Organic Monolayers," *J. Am. Chem. Soc.* 112:558-569 (1990), which are hereby incorporated by reference in their entirety) and the Staudinger ligation approach (Soellner et al., "Site-Specific Protein Immobilization by Staudinger Ligation," *J. Am. Chem. Soc.* 125:11790-11791 (2003), which is hereby incorporated by reference in its entirety), the mechanism of surface attachment is the nucleophilic attack on the surface-bound moiety by the probe molecule of interest (i.e. thiol- or amine-terminated oligonucleotide or protein).

In the case of protein arrays, solution additives are very often required to keep the probe spot hydrated during immobilization (Wang et al., "Microarray-Based Detection of Protein Binding and Functionality by Gold Nanoparticle Probes," *Anal. Chem.* 77:5770-5774 (2005)) and to aid in the homogenous distribution of molecules (Deng et al., "Transport at the Air/Water Interface is the Reason for Rings in Protein Microarrays," *J. Am. Chem. Soc.* 128:2768-2769 (2006)). This second function of an additive is vital for the removal of "coffee stain" rings (Deegan et al., "Capillary Flow as the Cause of Ring Stains from Dried Liquid props," *Nature* 389:827-829 (1997)) and bright center spots, which are presumably the result of the physisorption of molecules from the solution's initial contact with the surface.

Commonly used additives—glycerol, polyethylene glycol, trehalose, and surfactants—unfortunately contain reactive groups themselves (Wu et al., "Comparison of Hydroxylated Print Additives on Antibody Microarray Performance," *J. Proteome Res.* 5:2956-2965 (2006)). These include the hydroxyls on glycerol (Olle et al., "Comparison of Antibody Array Substrates and the use of Glycerol to Normalize Spot Morphology," *Exp. Mol. Pathol.* 79:206-209 (2005)), trehalose (Kusnezow et al., "Antibody Microarrays: An Evaluation of Production Parameters," *Proteomics* 3:254-264 (2003)), polyethylene glycol (Wu et al., "Comparison of Hydroxylated Print Additives on Antibody Microarray Performance," *J. Proteome Res.* 5:2956-2965 (2006); Wu et al., "DNA and Protein Microarray Printing on Silicon Nitride Waveguide Surfaces," *Biosensors and Bioelectronics* 21:1252-1263 (2006)), and many surfactants (Deng et al., "Transport at the Air/Water Interface is the Reason for Rings in Protein Microarrays," *J. Am. Chem. Soc.* 128:2768-2769 (2006); Wu et al., "DNA and Protein Microarray Printing on Silicon Nitride Waveguide Surfaces," *Biosensors and Bioelectronics* 21:1252-1263 (2006); Liu et al., "Optimization of Printing Buffer for Protein Microarrays Based on Aldehyde-Modified Glass Slides," *Frontiers in Bioscience* 12:3768-3773 (2007)).

In the context of developing methodology for preparing antibody arrays for use with Arrayed Imaging Reflectometry ("AIR") protein detection technique, it was observed that glycerol in particular interfered with antibody immobilization on glutaraldehyde-coated surfaces. While the precise structure of surface-immobilized glutaraldehyde is not well understood, solution-phase experiments (Migneault et al., "Glutaraldehyde: Behavior in Aqueous Solution, Reaction with Proteins, and Application to Enzyme Crosslinking," *BioTechniques* 37:790-802 (2004)) indicate that it is likely polymerized to some extent, providing both saturated and α,β-unsaturated aldehyde functionality for carbonyl- and Michael-addition of reactive amines. Although the reaction of aldehydes with alcohols, such as glycerol, to form hemiacetals and acetals is reversible, the neutral to slightly basic pH employed for protein immobilization provides enhanced stability for acetals (particularly cyclic), while reducing the rate of imine formation (the desired reaction in this case) (Jencks, "Studies on the Mechanism of Oxime and Semicarbazone Formation," *J. Am. Chem. Soc.* 81:475-481 (1959)). In fact, as demonstrated in the Examples presented infra, it has been confirmed via NMR spectroscopy that the concentration of glycerol typically employed in protein spotting solutions efficiently hinders reaction between glutaraldehyde and butylamine (a model amine) in MPBS-d at pH 7.2.

Because the amount of immobilized probe correlates with assay performance, and probe spotting becomes inefficient with most currently used additives, to improve assay performance it would be desirable to identify additives that will not participate in a nucleophilic attachment protocol (and circumvent competition for surface reactive groups) but will operate to remove surface morphological anomalies on the resulting chip.

The present invention is directed to overcoming these and other deficiencies in the art.

SUMMARY OF THE INVENTION

A first aspect of the present invention relates to a method of coupling a reactant (or probe precursor) to a functionalized surface for purposes of forming an arrayed sensor. This method includes the steps of: providing a surface having a reactive functional group; and introducing onto the surface, at a plurality of discrete locations, two or more compositions that include a different reactant (probe precursor) and a non-nucleophilic additive, wherein such introduction is carried out under conditions effective to allow for covalent binding of the reactant to the surface via the reactive functional group. This results in a probe-functionalized array that substantially overcomes the problem of surface morphological anomalies on the array surface.

According to one embodiment, the non-nucleophilic additive has a structure according to formula (I) as follows:

(I)

where n is an integer from 0 to about 250; m is an integer from 1 to about 3; and $R^1$ and $R^2$ are independently selected from the group of a C1 to C3 alkyl, or $R^1$ and $R^2$ together form a C1 to C3 alkyl, in which case the compound of formula (I) has a cyclic structure.

According to another embodiment, the non-nucleophilic additive is dimethylsulfoxide.

A second aspect of the present invention relates to a solution or formulation suitable for coupling a probe molecule onto an array surface (i.e., for preparing the probe-functionalized spots on an arrayed chip). The formulation, preferably in the form of an aqueous solution, includes a reactant molecule (or probe precursor), which upon binding to an array surface forms a probe molecule; and an effective amount of a non-nucleophilic additive. The amount of the non-nucleophilic additive is such that the formulation promotes substantially homogeneous distribution of the probe molecule on the array surface.

A third aspect of the present invention relates to an array having a surface with a plurality of capture probes coupled to the surface at a plurality of discrete locations, wherein the array is prepared according to a method according to the first aspect of the present invention or using one or more solutions according to the second aspect of the present invention.

A fourth aspect of the present invention relates to a method for detecting the presence of a target molecule using a capture probe. This method includes the steps of: providing an array according to the third aspect of the present invention; exposing the array to a sample; and then detecting a change in a property of the array at one or more of the plurality of discrete locations, wherein the property change indicates specific binding of a target molecule to the capture molecule.

The arrays of the present invention are suitable for use with any of a variety of optical detection systems, and therefore a number of array properties can be assessed depending upon the type of detection system utilized. Exemplary optical detection systems include, without limitation fluorescence imaging systems, ellipsometry systems, surface plasmon resonance (SPR) systems, including both fluorescence and imaging SPR systems, arrayed imaging reflectometry (AIR) systems, Brewster angle straddle interferometry (BASI) systems, and microarray scanners. Any of a number of other suitable detection systems can also be employed.

The benefit of employing the non-nucleophilic additives, which do not participate in the chemical coupling of a reactant (or probe precursor) to the functionalized chip substrate, is that the additives promote better dispersion of the probe molecules across their respective discrete locations on the array. This improved dispersion consequently minimizes or entirely avoids the presence of surface morphological anomalies that can decrease the sensitivity of the detection system. As a result, improved sensitivity for the detection of target molecules can be achieved.

BRIEF DESCRIPTION OF THE DRAWINGS

FIG. 4 is a schematic of the manual array used for AIR additive experiments. Except for the control spots, which were comprised of α-fluorescein in 0.1% 12-crown-4 as a standard, all spots are anti-human IgG diluted in spotting buffer containing the specified percentage of an additive. "3×" indicates that each condition was spotted in triplicate.

FIGS. 5A-F illustrate representative AIR images of a chip taken by scanning through five different focal planes ((a) through (e)), and a composite image (f). The array includes control anti-fluorescein spots (leftmost column), and anti-human IgG spots diluted in either MPBS alone (second column from left) or varying concentrations of DMSO as additive (1%, 0.1% and 0.01% from left to right). The aspect ratio of the images has been altered to concisely display each focal slice.

FIG. 6A contains image of representative spots from an AIR array acquired at a 30 ms exposure time. The array consists of three replicates (only one shown in the figure) of anti-human IgG diluted in various concentrations of 12-crown-4-containing buffer and an anti-fluorescein control. FIGS. 6B-C are histograms that depict the area intensity profiles of a spot arrayed with MPBS alone and with 0.1% of 12-crown-4, respectively.

DETAILED DESCRIPTION OF THE INVENTION

Figure 1:
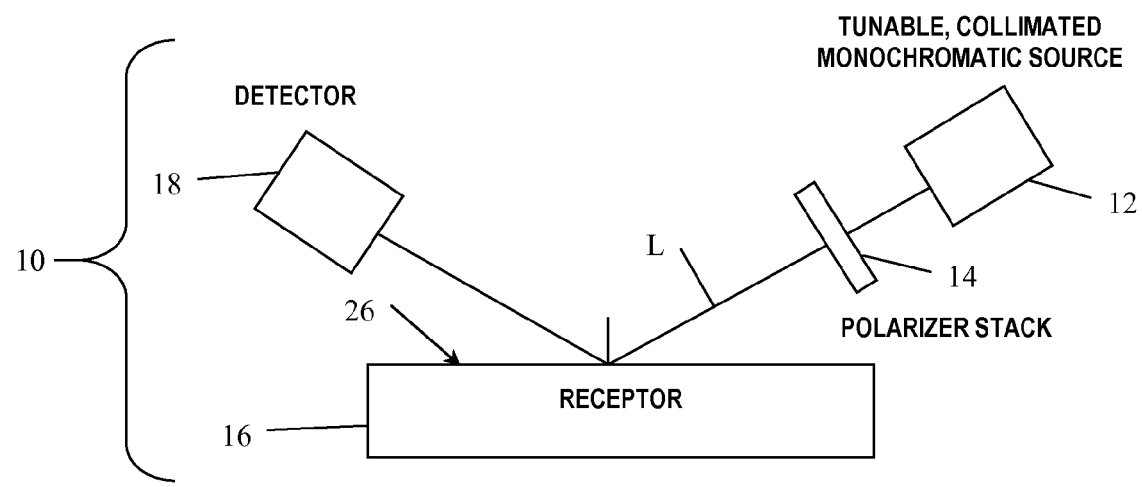
FIG. 1 is a schematic illustration of an AIR detection system.

The present invention relates to formulations and methods for the preparation of probe arrays, as well as the resulting arrays prepared using these materials, and the use of such arrays.

As used herein, the term "probe" refers to a molecule or molecular complex capable of binding specifically and selectively to one or more target molecules whose presence in a sample is being queried with a particular sensor array. The term "probe precursor" refers to a molecule or molecular complex prior to its binding to the chip substrate, i.e., the probe precursor is a solution phase reactant that is intended to be coupled to the substrate at discrete locations.

The formulations of the invention are intended to be used for coupling of a reactant (or probe precursor) to the substrate (of the array chip), preferably a functionalized surface of the substrate that contains one or more reactive functional groups that are receptive to coupling with the reactant at discrete locations on the surface. These discrete locations are known in the art simply as "spots."

The formulations of the present invention include a solvent, a reactant (or probe precursor), and an effective amount of a non-nucleophilic additive.

Because the reactants (probe precursors) are typically, though not exclusively, directed to biological target molecules, the reactants are most stable in aqueous solutions. Thus, the solvent is preferably water or an aqueous solution. The aqueous solution may also contain buffer salts as commonly used in the art.

The reactant preferably includes a probe molecule that allows for specific and selective binding to a target molecule, and a functional group that binds to or reacts with the reactive functional group on the substrate surface (discussed hereinafter). Exemplary functional groups include primary amines, carboxylic acids, thiols, aldehydes, or primary alcohols. Preferably, only a single type of functional group is used in a single probe formulation.

Exemplary reactants include, without limitation, peptides or polypeptides, amine-containing nucleic acid molecules (e.g., $NH_2$-oligo or oligo-$NH_2$), protein nucleic acid (PNA) molecules, and peptidomimetic compounds or small molecule compounds that include an amine group. Suitable peptides or polypeptides include, without limitation, peptide fragments, protein macromolecules, an antibody or antibody fragment, or a viruslike particle or subcapsid assembly thereof.

A trait inherent to all biosensors, regardless of labeling status or means of signal transduction, is probe immobilization. The role of the terminal hydroxyl of a silicon dioxide surface is highly flexible as it may act as a nucleophile (Bikiaris et al., "Compatibilisation Effect of PP-g-MA Copolymer on iPP/$SiO_2$ Nanocomposites Prepared by Melt Mixing," *Eur. Polym. J.* 41:1965-1978 (2005); Tripp et al., "Chemical Attachment of Chlorosilanes to Silica: A Two-Step Amine-Promoted Reaction," *J. Phys. Chem.* 97:5693-5698 (1993), which are hereby incorporated by reference in their entirety) or support adsorption. For this reason, silicon dioxide is readily derivatized through a variety of chemical methods. These chemical reactions result in the effective transformation of the hydroxyl group to any of a number of chemical functionalities including, but not limited to, amines (Huang et al., "Directed Assembly of One-Dimensional Nanostructures into Functional Networks," *Science* 291:630-633 (2001), which is hereby incorporated by reference in its entirety) or halides (Hergenrother et al., "Small-Molecule Microarrays: Covalent Attachment and Screening of Alcohol-Containing Small Molecules on Glass Slides," *J. Am. Chem. Soc.* 122: 7849-7850 (2001), which is hereby incorporated by reference in its entirety). From each initial reaction, a secondary chemical can be added to further alter the surface reactivity or probes may be directly coupled. Moreover, a multitude of functionalized silanes, molecules that couple to and self-assemble on silicon dioxide (Onclin et al., "Engineering Silicon Oxide Surfaces Using Self-Assembled Monolayers," *Angew. Chemie Int. Ed.* 44:2-24 (2005), which are hereby incorporated by reference in their entirety), are commercially available, and may confer a diverse chemical landscape to the surface of the substrate (e.g., amines, epoxides, alkenes). This is by no means a comprehensive discussion of surface immobilization protocols, but probe layer formation strategy is an important topic for any biosensor. A number of these approaches are generally described in U.S. Pat. No. 7,226,733 to Chan et al. and U.S. Pat. No. 7,292,349 to Miller et al., which are hereby incorporated by reference in their entirety.

Typically, protein arrays are used in conjunction with target molecules conjugated with a fluorophore or other reporter element (MacBeath, "Protein Microarrays and Proteomics," *Nat. Genet.* 32(Suppl 2):526-532 (2002); Boutell et al., "Functional Protein Microarrays for Parallel Characterisation of p53 mutants," *Proteomics* 4:1950-1958 (2004), which are hereby incorporated by reference in their entirety) or as sandwich assays with labeled antibodies. While these methods have yielded valuable data, label-free protein detection techniques have generated considerable interest as alternatives, due to their potential to simplify and improve the accuracy of the assay process.

Amine terminated probes—certain small molecules, synthesized oligonucleotides, peptides, antibodies—can be immobilized to the silicon dioxide surface in a variety of ways. As described in the accompanying examples, an amine-terminated alkoxysilane (γ-aminopropyl triethoxysilane, APTES) is used to tether a homo-bifunctional crosslinker (glutaraldehyde) to the surface. This leaves a terminal aldehyde to react with a free amine on the probe, forming an imine. Imines are reversible in solution (Huc et al., "Virtual Combinatorial Libraries: Dynamic Generation of Molecular and Supramolecular Diversity by Self-Assembly," *Proc. Natl. Acad. Sci. USA* 94:2106-2110 (1997), which is hereby incorporated by reference in its entirety), but upon the assembly of the probe layer, they become effectively solvent inaccessible, and, therefore, stable. Other homo-bifunctional crosslinkers that utilize an amino-silanized surface are disuccinimidyl carbonate (DSC) and p-phenylene diisothiocyanate (PITC) (Macbeath et al., "Printing Proteins as Microarrays for High-Throughput Function Determination," *Science* 289:1760-1763 (2000); Guo et al., "Direct Fluorescence Analysis of Genetic Polymorphisms by Hybridization with Oligonucleotide Arrays on Glass Supports," *Nucleic Acids Res.* 22:5456-5465 (1994), which are hereby incorporated by reference in their entirety). As an alternate route, the resulting surface amine after the addition of APTES may be reacted with succinic anhydride to yield a terminal carboxylic acid (Diehl et al., "Manufacturing DNA Microarrays of High Spot Homogeneity and Reduced Background Signal," *Nucleic Acids Res.* 29:e38 (2001), which is hereby incorporated by reference in its entirety). From here any carbodiimide (e.g., EDC or DCC) or combination of carbodiimide and N-hydroxysuccinimide (NHS) will activate the carboxylic acid (Jeong et al., "Novel Polymer-DNA Hybrid Polymeric Micelles Composed of Hydrophobic Poly(D,L-lactic-co-glycolic acid) and Hydrophilic Oligonucleotides," *Bioconjugate Chem.* 12:917-923 (2001); Nedelkov et al., "Analysis of Native Proteins from Biological Fluids by Biomolecular Interaction Analysis Mass Spectrometry (BIA/MS): Exploring the Limit of Detection, Identification of Non-Specific Binding and Detection of Multi-Protein Complexes," *Biosens. Bioelectron.* 16:1071-1078 (2001), which are hereby incorporated by reference in their entirety). The activated ester is now primed for attack by a free amine, which results in the formation of a stable amide bond.

A more direct coupling to the $SiO_2$ surface is completed through the nucleophile-mediated displacement of a halide formed by a surface reaction with thionyl chloride. This approach is described, for example, in U.S. Pat. No. 7,226,733 to Chan et al. and U.S. Pat. No. 7,292,349 to Miller et al., which are hereby incorporated by reference in their entirety. While this approach was used for the attachment of alcohols, it has been experienced that this approach works well with amines as well. One caveat of this approach is the high localized surface concentration of hydrochloric acid that is released upon probe immobilization.

Biotinylated molecules are also prevalent as biomolecular probes. To immobilize molecules of this class, a layer of avidin or streptavidin is first attached to the surface. This can be accomplished in one of two ways: direct coupling of avidin to the surface or a primary layer of biotin as a tether. Routes to the former have been covered above; the latter method is accomplished through manipulations of biotin's terminal carboxylic acid. The briefly described carboxylic acid activation schemes hold here, but an alternative, synthetic biotin called sulfo-NHS biotin may be used to couple directly to the APTES-generated surface amine (Ouyang et al., "Macroporous Silicon Microcavities for Macromolecule Detection," *Adv. Funct. Mater.* 15:1851-1859 (2005), which is hereby incorporated by reference in its entirety). From this biotin monolayer, avidin will specifically assemble on the surface. As a homotetramer, binding four molecules of biotin per molecule of avidin (Chilkoti et al., "Site-Directed Mutagenesis Studies of the High-Affinity Streptavidin-Biotin Complex: Contributions of Tryptophan Residues 79, 108, and 120," *Proc. Natl. Acad. Soc. USA* 92:1754-1758 (1995), which is hereby incorporated by reference in its entirety), biotinylated probes will readily immobilize on this layer. The biotin-avidin complex is reversible under thermodynamic control, but, due to the extremely high affinity, the interaction is considered approximately covalent under most experimental conditions. Other epitope-based scaffolds could be used; however, such as $Ni^{2+}$-NTA for His6-tags (Zhu et al., "Global Analysis of Protein Activities Using Proteome Chips," *Science* 293:2101-2105 (2001), which is hereby incorporated by reference in its entirety), GSH for glutathione-5-transferase tags (Kawahashi et al., "In vitro Protein Microarrays for Detecting Protein-Protein Interactions: Application of a New Method for Fluorescence Labeling of Proteins," *Proteomics* 3:1236-1243 (2003), which is hereby incorporated by reference in its entirety), anti-epitope antibodies (e.g., for myc-tags) (Wingren et al., "Microarrays Based on affinity-Tagged Single Chain Fv Antibodies: Sensitive Detection of Analyte in Complex Proteomes," *Proteomics* 5:1281-1291 (2005), which is hereby incorporated by reference in its entirety), and others (see Tomizaki et al., "Protein-Detecting Microarrays: Current Accomplishments and Requirements," *Chem. Bio. Chem.* 6:782-799 (2005), which is hereby incorporated by reference in its entirety).

Importantly, the non-nucleophilic additive facilitates dispersion of the reactant (probe precursor) within the composition but does not participate in covalent bond formation between the functionalized chip surface and the reactive functional group of the reactant.

One embodiment of the non-nucleophilic additive has a structure of formula (I) as follows:

$$R^1 \text{—} O \text{—} [(CH_2)_m O]_n \text{—} R^2 \qquad (I)$$

where, n is an integer from 0 to about 250; m is an integer from 1 to 3, preferably 1 or 2; and $R^1$ and $R^2$ are independently selected from the group of a C1 to C3 alkyl, or $R^1$ and $R^2$ together form a C1 to C3 alkyl, in which case the compound of formula (I) has a cyclic structure. $R^1$ and $R^2$ are preferably methyl or ethyl, or together form an ethyl group.

Preferably, the non-nucleophilic additive of formula (I) has a molecular weight that is about 5000 Da or less, more preferably about 4000 Da or less, or about 3000 Da or less, most preferably about 2000 Da or less, or even about 1000 Da or less.

Exemplary non-nucleophilic additives of formula (I) include, without limitation, crown ethers (18-Crown-6,15-Crown-5, 12 Crown-4, etc.), bis(2-methoxyethyl)ether, dialkyl ethers, and polyethylene glycol dialkyl ether.

According to another embodiment, the non-nucleophilic additive is dimethylsulfoxide (DMSO).

The non-nucleophilic additive is present in the formulation in an amount effective to avoid or reduce the severity of surface morphological anomalies caused by non-homogeneous distribution of the reactant across a spot on the array where the reactant is bound. These surface morphological anomalies include, as noted above, bright center spots and "coffee stain" rings (or halos) that can interfere with accurate detection of target molecule binding at a particular spot. In other words, the use of effective amounts of the non-nucleophilic additive promotes substantially homogeneous distribution of the reactant across each of the spots on the array where the probe is located. As used herein, "avoid or reduce the severity" is intended to mean that the reduction is by way of comparison to an otherwise identical formulation that lacks the non-nucleophilic additive. By homogeneous distribution, it is intended that the variance of reactant concentration across the surface of a spot is minimized (relative to spots prepared in the absence of the non-nucleophilic additives). Stated another way, there is preferably less than about 20 percent pixel variation across the array spot, more preferably less than about 15 percent, most preferably less than about 10 percent pixel variation. Under optimal conditions, the non-nucleophilic additive may reduce pixel variation across the array spot to less than about 5 percent variation, more preferably less than about 3 percent variation, or most preferably less than about 1 percent variation.

Any effective amount of non-nucleophilic additive can be used. Typically, such an effective amount is between about 0.001 to about 3 percent v/v, more preferably between about 0.01 to about 1 percent v/v.

The formulations of the present invention are preferably prepared immediately prior to their use for coupling of a reactant to an array surface. If the formulations are to be stored for longer than several weeks before use, then it is also possible to introduce one or more preservatives to avoid contamination of the array surface with microorganisms. Preservatives that do not interfere with the coupling chemistry are preferred. A number of such preservatives are known in the art (e.g., sodium azide, citric acid, sodium benzoate, and sodium ethylmercurithiosalicylate (thimerasol)).

Different formulations, containing different reactants, are intended to be used at discrete locations on the substrate to form the spots on the array. These different formulations may contain the same non-nucleophilic additive or different non-nucleophilic additives.

The substrate surface is preferably fabricated to possess one or more reactive functional groups that are receptive to covalent bonding to a reactant (or probe precursor) at each of the spots. Exemplary reactive functional groups include, without limitation, aldehyde, activated ester, isothiocyanate, azide, alkyne, silyl halide, and combinations thereof. Portions of the substrate surface that are not intended to contain a reactive functional group can be masked prior to introducing the reactant-containing formulation to the substrate surface.

An array can be prepared by introducing formulations of the present invention to the various discrete locations across the surface of the substrate, allowing sufficient time for covalent bond formation between the reactant (or probe precursor) and the reactive functional group, and then washing the surface of the thus-formed array in a manner effective to remove non-specifically bound reactant and any other impurities. Introduction of the formulations can be carried out by hand or machine, for example, a microarray printer. Suitable wash solutions are buffered saline solutions, including without limitation, phosphate buffered saline (pH 7.2), and HEPES buffer (pH 7.2). The array can then be used immediately or packaged under conditions effective to preserve the structure of the array for later use.

The overall design and construction of the array can be varied according to the particular detection system in which it is to be employed. These include, for example and without limitation, sensor arrays designed for use with AIR detection systems, SPR detection systems, BASI detection systems, and ellipsometry detection systems, as well as any other label-free or fluorescence labeled array detection technique.

The development of Arrayed Imaging Reflectometry (AIR), a label-free, optical biosensor, has been previously reported (Lu et al., "Reflective Interferometric Detection of Label-Free Oligonucleotides," *Anal. Chem.* 76:4416-4420

(2004); Mace et al., "Theoretical and Experimental Analysis of Arrayed Imaging Reflectometry as a Sensitive Proteomics Technique," *Anal. Chem.* 78:5578-5583 (2006), which are hereby incorporated by reference in their entirety). In one embodiment, the AIR technique creates a condition of near zero reflectance through an antireflective coating consisting of a thin film of silicon dioxide and covalently linked probe molecules; perturbation of this coating arises through the thickness increase that is concomitant with a biomolecular recognition event. Imaging near a reflectance zero confers a large dynamic range, and, as such, AIR is capable of easily detecting sub-Angstrom thickness increases. AIR is therefore exceptionally responsive to subtle surface immobilization inhomogeneities, much more so than typical fluorescence-based imaging methods. Through the utilization of AIR in the Examples, it was possible to investigate concurrently the immobilization profiles of a model antibody, anti-human IgG, over a range of additive conditions and concentrations, as well as confirm the activity of the antibody in each additive.

An AIR detection system is described in U.S. Pat. No. 7,292,349 to Miller et al., which is hereby incorporated by reference in its entirety. This system is illustrated in FIG. 1. The system 10 includes a light source 12, a polarizer 14, a receptor 16 (i.e., the functionalized sensor chip of the present invention), and a detector 18. The light source 12 generates and transmits light (L) at a set wavelength towards a surface of the receptor. One or more lenses and filters can be employed to optimize the system. AIR exploits interference between reflections from the medium/coating and coating/substrate interfaces on the receptor, exhibiting changes in reflectivity upon binding of biomolecules to the coating. In practice, using a silicon wafer having an oxide coating, judicious choice of incident angle and wavelength can be used with s-polarized light to obtain near complete destructive interference (i.e., reflectivity that is preferably less than about $10^{-5}$ or even $10^{-6}$ under some circumstances) in the absence of a target molecule. The condition of near complete (or near perfect) destructive interference is removed upon target binding. Thus, highly sensitive detection of even small quantities of any target is possible.

While AIR using s-polarized light has proven to be a highly sensitive, simple analytical method for the quantitative detection of a variety of biomolecular analytes, the system described in the above-referenced U.S. Pat. No. 7,292,349 to Miller et al. is much more easily carried out in a dry state, that is, with an air/oxide interface rather than with an aqueous/oxide interface. An improved system for performing AIR in an aqueous environment is described in co-pending U.S. patent application Ser. No. 12/261,818 to Mace et al., and PCT International Patent Application No. PCT/2008/081804 to Mace et al., which are hereby incorporated by reference in their entirety. Basically, the flow cell as described therein allows for coupling of the s-polarized light into the aqueous environment for detection of target binding. Use of this same flow cell, containing a sensor chip functionalized in accordance with the present invention, is contemplated herein.

In both the wet and dry AIR systems, the sensor chip has the same fundamental construction, with a substrate, one or more coating layers on the substrate, and then the reactant (probe molecule) bound to the coating surface. As described in the above-referenced U.S. Pat. No. 7,292,349 to Miller et al., U.S. patent application Ser. No. 12/261,818 to Mace et al., and PCT International Patent Application No. PCT/2008/081804 to Mace et al., a number of different materials can be selected for the substrate and coating(s). Any suitable combination of substrates and coatings is contemplated for the sensor array to be used in an AIR detection system.

The BASI detection system is described in U.S. Pat. No. 7,551,294 to Rothberg, which is hereby incorporated by reference in its entirety. The BASI system, like the AIR system, exploits interference between reflections from the medium/coating and coating/substrate interfaces, and exhibits changes in reflectivity upon binding of biomolecules to the coating. The basic design of the system is similar to that illustrated in FIG. 1 (for AIR), but the structure of the sensor chip differs. The BASI system is functional with any substrate/coating combinations where the coating is very thin (e.g., a native oxide film on silicon) and when the incidence angle on one of two interfaces (substrate/coating or coating/medium) is greater than its Brewster angle and the incidence angle on the other of the two interfaces is less than its Brewster angle. Unlike AIR systems being commercially developed for use with incident s-polarized light, the BASI system relies on the detection of p-polarized light. As a result of using Brewster angle straddle and p-polarized light, a phase flip of the reflected polarization allows nearly complete destructive interference. As with the AIR detection system, sensitive detection of even small quantities of target molecules is possible.

Figure 2:
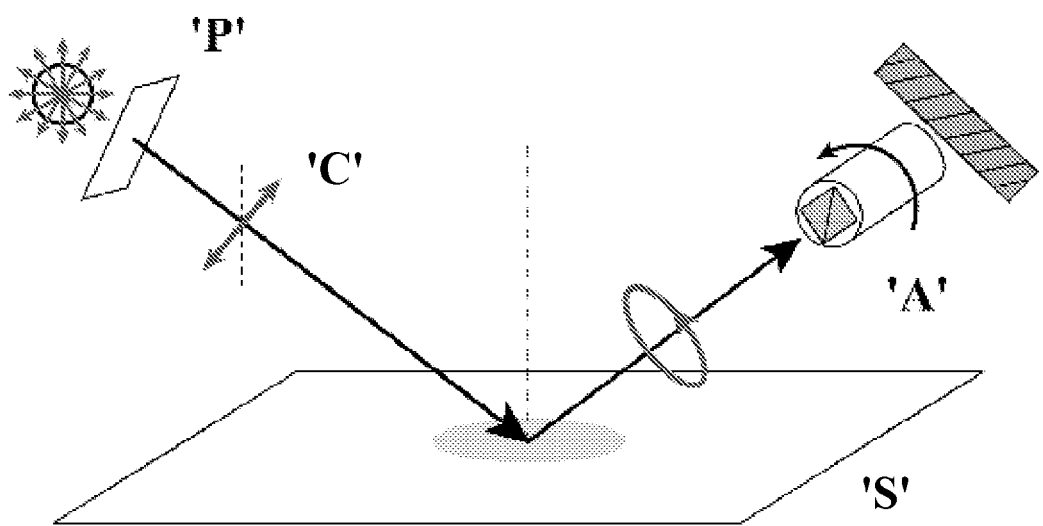
FIG. 2 is a schematic illustration of an ellipsometry detection system.

Ellipsometric detection systems measure the polarization component of reflected light as a measure of changes in coating thickness on the surface of the sensor chip. Ellipsometry sensitively measures the change of the state of polarization when electromagnetic radiation is reflected or transmitted by a sample. A classical embodiment of such an ellipsometric detection system, illustrated in FIG. 2, includes a light source that emits a collimated light beam passing a variable polarization controller given by the combination of a linear polarizer (P) and a compensator in the form of a quarter-wave plate (C). The polarized light beam is incident on the sensor surface (S) under a known oblique angle, reflected from the sample surface and analyzed by a second linear polarizer coupled to a suitable photodetector (A, collectively). In this ellipsometer setup, the measurement may be done by changing the azimuths of the components P and A, while the optical axis of C is kept at a constant azimuth, e.g., at 45° with respect to the plane of incidence, until the photodetector receives a minimum of intensity. The azimuthal angles of the components P, C and A for this "nulling" condition may be used to calculate the ellipsometric angles Delta and Psi, which are specific for the optical parameters of the sample at a given angle of incidence and wavelength of light. Using a suitable optical model and numerical regression, the quantities Delta and Psi may be recalculated in terms of the thickness of the optical layer, or changes thereof during a growth process. The application of ellipsometry for monitoring of binding reactions of biological molecules dates back to 1942 (Rothen et al., "Serological Reactions of Protein Films and Denatured Proteins," *J. Exp. Med.* 76:437-450 (1942), which is hereby incorporated by reference in its entirety), where the amount of adsorbed biological material at a surface during a binding reaction may be recalculated from the quantities Delta and Psi.

Imaging ellipsometry, as described for example in U.S. Pat. No. 5,076,696 to Cohn et al., which is hereby incorporated by reference in its entirety, uses spatially resolving detector and imaging optics to allow for a massively parallel measurement of ellipsometric data, e.g., in the form of Delta and/or Psi maps. Such maps may in turn be converted into surface maps of layer thickness, optical index of refraction, chemical composition or the amount of adsorbed material for each spot on an array. Imaging ellipsometry with its intrinsic parallel detection scheme may be used advantageously as a detection technique for these so-called biochips, microarrays or microplates (Eing et al., *Imaging Ellipsometry in Biotechnology*, ISBN 3-9807279-6-3 (2002), which is hereby incorporated by reference in its entirety).

Imaging ellipsometry has been demonstrated with light employed for the measurement impinging on the surface to be measured coming from the ambient medium. Other measurement setups are based on total internal reflection as described, for example, in U.S. Pat. No. 6,594,011 to Kempen, which is hereby incorporated by reference in its entirety. Here, the light from a light source is directed through an internal reflection element to reflect off the specimen to be detected.

Figure 3A:
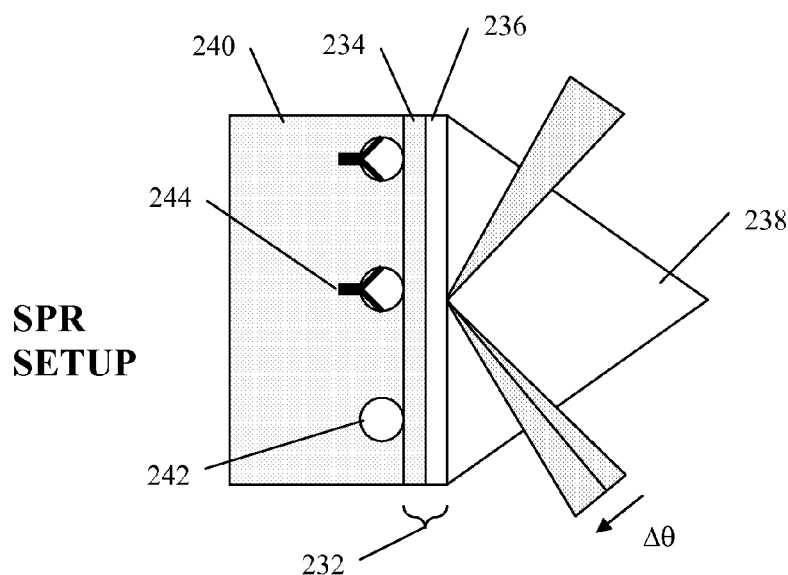
FIG. 3A is a schematic illustration of an SPR detection system.
Figure 3B:
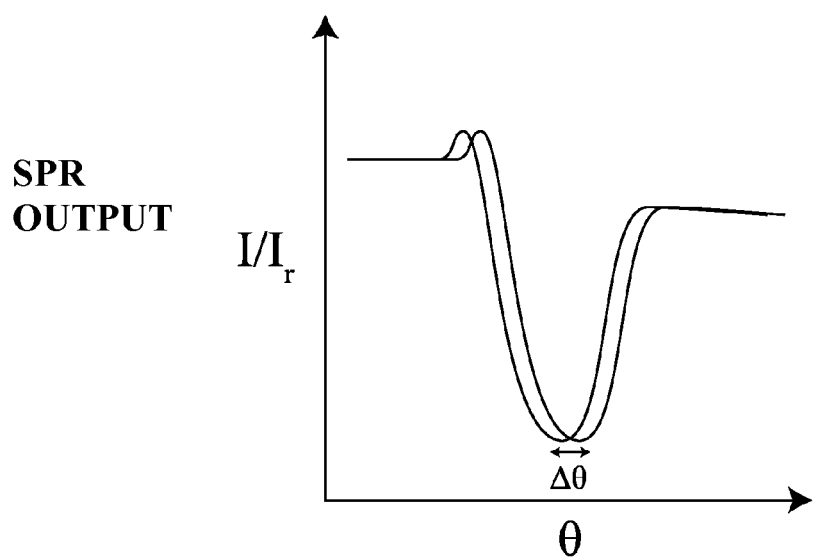
FIG. 3B illustrates the output of SPR.

Enhancement of the detection signal can be achieved using SPR ellipsometry, illustrated in FIG. 3A. The substrate 32 employed during SPR ellipsometry uses a thin metal layer 34 to allow the excitation and propagation of surface plasmons. While one side of the metal layer 34 is in contact with a transparent support structure 36, usually attached to a prism 38 allowing light to couple-in under an oblique angle, the other side of the layer is exposed to the ambient medium 40. Changes in the optical index of refraction in the ambient by the formation of an adsorbent layer (e.g., target molecule binding to surface-bound probe molecules 42) are monitored as a shift in the angle of incidence ($\Delta\theta$) that generates surface plasmon resonance, causing a change of reflected light intensity (see FIG. 3B). For SPR based sensors it is known that an intermediate dielectric layer between the metal film and the probed surface may act as a means to further increase the sensitivity. SPR can be performed using fluorescence SPR or imaging SPR.

One exemplary SPR substrate is described in U.S. Pat. No. 7,332,329 to Wark et al., which is hereby incorporated by reference in its entirety. This SPR substrate is particularly suited for biomolecular arrays for detection of target molecules, where the substrate includes a plurality of a metallic islands surrounded by a hydrophobic layer or a dielectric material, and the probe molecules (reactants) are bound to the metallic islands.

The arrays of the invention are intended to be used for the detection of suitable target molecules of the types noted above. Typically, the array is exposed to a sample for a sufficient duration to allow specific binding between a surface-bound probe molecule and any target molecule(s) present in the sample. After washing the array to remove non-specifically bound target molecule(s), the array can be read with any suitable detection system. The detection systems identify a change in a property of the array at one or more spots, and this property change indicates specific binding of a target molecule to the capture molecule. Control spots can also be utilized to identify false positive or false negative binding events.

The property change to be detected can be the presence of a fluorescent label (where the label is tethered to the target molecule itself or a secondary reagent, such as an antibody or binding fragment thereof). Alternatively, the property change can be one that does not involve a separate label. Exemplary label-less approaches include, without limitation, detection of a change in the thickness of the coating at a particular spot, a change in the local refractive index at a particular spot, and the reflectivity of light at a particular spot. The methods for detecting the presence of a target molecule can be carried out by ellipsometry, AIR, BASI, or SPR ellipsometry.

In the present invention, the detecting of target molecule binding is improved, because the presence of surface morphological anomalies is minimized. Such anomalies include a corona or "coffee stain" about the perimeter of an array spot or a bright central feature of the spot, both of which are known to interfere with accurate detection and quantification. The arrays prepared in accordance with the present invention are preferably characterized by the absence or significant reduction in the corona or bright central feature (as compared to a capture molecule bound to a spot in the absence of the non-nucleophilic additive). This should result in improved accuracy of the detection and quantification of target molecule binding to the array surface.

EXAMPLES

The Examples set forth below are for illustrative purposes only and are not intended to limit, in any way, the scope of the present invention. The following materials were used in the accompanying Examples.

Silicon wafers (n-type, <100>) with ~1400 Å of thermally grown silicon dioxide were obtained from the Rochester Institute of Technology. All experiments were carried out on chips derived from the same batch of wafers. Aminopropyl triethoxysilane (APTES, SigmaAldrich) and glutaraldehyde (50% aqueous solution, Alfa Aesar) were used for chip functionalization. Anti-human IgG was obtained from GeneTex Inc. (GTX 77542), and human IgG was obtained from SigmaAldrich.

The following additives were tested at 1%, 0.1% and 0.01% (v/v unless otherwise stated): 12-crown-4 (SigmaAldrich), 18-crown-6 (w/v, Alfa Aesar), diethyl ether (Fisher Scientific), diglyme (TCI America), dimethyl sulfoxide ("DMSO", Fisher Scientific), polyethylene glycol dimethyl ether, ~Mw=2 kDa (w/v, "PEG-DME", SigmaAldrich). Glycerol (Mallinckrodt Baker Inc.) at final concentrations of 20%, 2% and 0.2%, and Triton-X 100 (SigmaAldrich) at final concentrations of 0.1%, 0.01% and 0.001% were also tested. Concentrations of glycerol and Triton-X 100 were chosen based on commonly used protocols found in the literature (MacBeath et al., "Printing Proteins as Microarrays for High-Throughput Function Determination," *Science* 289:1760-1763 (2000); Deng et al., "Transport at the Air/Water Interface is the Reason for Rings in Protein Microarrays," *J. Am. Chem. Soc.* 128:2768-2769 (2006); Olle et al., "Comparison of Antibody Array Substrates and the use of Glycerol to Normalize Spot Morphology," *Exp. Mol. Pathol.* 79:206-209 (2005); Liu et al., "Optimization of Printing Buffer for Protein Microarrays Based on Aldehyde-Modified Glass Slides," *Frontiers in Bioscience* 12:3768-3773 (2007), which are hereby incorporated by reference in their entirety).

Variants of ethylene glycol were selected as the basis set of additives because polyethylene glycols are ubiquitously used in protein crystallography screens (presumably inert with respect to the protein) (Radaev et al., "A Survey of Protein-Protein Complex Crystallizations," *Acta. Cryst.* D62:605-612 (2006); McPherson, A., "Crystallization of Proteins from Polyethylene Glycol," *J. Biol. Chem.* 251:6300-6303 (1976), which are hereby incorporated by reference in their entirety), and strongly resist adsorption to proteins (Ostuni et al., "A Survey of Structure—Property Relationships of Surfaces that Resist the Adsorption of Protein," *Langmuir* 17:5605-5620 (2001), which is hereby incorporated by reference in its entirety). However, since the terminal α- and ω-hydroxyls are nucleophilic, each ethylene glycol derivative was "capped" either by an alkoxy group or via cyclization. DMSO was chosen because it is commonly utilized in small molecule/protein interaction assays (Comley, J., "Methods and Principles in Medicinal Chemistry," in *High Throughput-Screening in Drug Discovery*, Vol. 35, Huser, J., ed., Weinheim, Germany:WILEY-VCH Verlag GmbH and Co., pp 50-51 (2006), which is hereby incorporated by reference in its entirety), and at low concentrations it does not appear to disrupt the structure of most proteins (Tjernberg et al., "DMSO Related Effects in Protein Characterization," *J. Biomol. Screen* 11:131-137 (2006); Bhattacharjya et al., "Effects of Organic Solvents on Protein Structures: Observation of a Structured Helical Core in Hen Egg-White Lysozyme in Aqueous Dimethylsulfoxide," *Protein Struct. Func. Genet.* 29:492-507 (1997), which are hereby incorporated by reference in their entirety). Triton X-100 and glycerol were used as controls due to their nearly universal use in the preparation of protein arrays.

Example 1

Detailed Surface Attachment Chemistry Protocol

Silicon wafers (n-type, <100>), with ~1400 Å of thermally grown silicon dioxide were obtained from Rochester Institute of Technology and diced into 2 cm×1 cm or 1 cm×1 cm chips for AIR experiments or ellipsometric measurements, respectively. Diced chips were etched in dilute hydrofluoric acid until their silicon dioxide thicknesses were 1380 Å, as measured by spectroscopic ellipsometry (J. A. Woollam M2000). The chips were then washed in a solution of 1:1 methanol:HCl for 30 minutes. The chips were then washed repeatedly with glass distilled deionized water (pH 6.0) ("ddH$_2$O") and dried under a stream of nitrogen. A solution of 0.4% v/v (γ-aminopropyl)triethoxysilane ("APTES") in anhydrous toluene was added to the chips and allowed to shake for 15 minutes (Vandenberg et al., "Structure of 3-Aminopropyl Triethoxy Silane on Silicon Oxide," *J. Colloid Interf. Sci.* 147:103-118 (1991), which is hereby incorporated by reference in its entirety). The chips were then washed repeatedly with ethanol, dried under a stream of nitrogen, and cured at 100° C. for 15 minutes. Once the chips had cooled to room temperature, a solution of 1.25% glutaraldehyde (50% aqueous) in MPBS buffer (aqueous buffer containing 10 mM NaH$_2$PO$_4$, 10 mM Na$_2$HPO$_4$, and 150 mM NaCl, at pH 7.2) was added to the chips and allowed to shake for 60 minutes. The chips were then washed repeatedly with ddH$_2$O, acetone, and ddH$_2$O again before being dried under a stream of nitrogen. At this point, the chips were functionalized to bear a terminal aldehyde to facilitate the general-amine immobilization of probe antibodies.

Probe antibodies were kept as two-fold stock concentrations in MPBS alone to facilitate dilutions into additive solutions. Likewise, all additives were kept as two-fold stocks, i.e. 0.2% additive in MPBS to give a final concentration of 0.1% v/v of the additive. Probe solutions were diluted into additives at the time of arraying only, and this was done to ensure the freshness of the sample and to limit any detrimental effects the additive may have on antibody function. The final solutions were manually arrayed, in a volume of 0.5 µL, onto the functionalized chips in a predetermined pattern (FIG. 4). This array was comprised of four differing anti-human IgG conditions at 500 µg/mL: in MPBS alone or MPBS plus 1%, 0.1%, or 0.01% of the additive under study; additionally, a set of anti-fluorescein negative control spots were arrayed at a final concentration of 300 µg/mL in 0.1% 12-crown-4. A lower concentration was used for anti-fluorescein to ensure that the effective layer thickness (observed in terms of spot reflectance in this case) was similar for the two antibody spots (32.1 Å for anti-human IgG and 30.1 Å for anti-fluorescein, as measured by spectroscopic ellipsometry), as this facilitated more accurate data analysis.

The following additives were tested at 1%, 0.1%, and 0.01%: 12-crown-4, 18-crown-6 (w/v), diethyl ether, diglyme, PEG-DME (w/v), and DMSO. Glycerol was tested at 20%, 2%, and 0.2%; and Triton X-100 was tested at 0.1%, 0.01%, and 0.001%.

After the arrays were completed, the chips were placed into a modified humidity chamber and allowed to incubate for 60 minutes at 4° C. The chips were then removed from the chamber and residual liquid on each spot was allowed to evaporate to reduce smearing. The chips were then immediately immersed into a solution of 200 µg/mL bovine serum albumin ("BSA") in HEPES-buffered saline ("HBS," an aqueous buffer containing 20 mM HEPES, 150 mM NaCl, at pH 7.2) and allowed to shake for 60 minutes. Afterwards, the chips were thoroughly washed with MPBS and the edges were blotted dry to wick excess buffer off of the surface. Note that there was a small volume of residual buffer remaining over the array, thus keeping the probe spots hydrated.

Example 2

Analysis of Chips by AIR and Ellipsometry

To the surface-modified chips of Example 1, the target solutions were added and allowed to incubate for 60 minutes. This, unfortunately and inherently, diluted the target solution in an unquantifiable manner. However, this happened uniformly across a given chip, and since the signal change for the additives' spots was eventually normalized to the change for the MPBS spots present on each chip, this did not affect the end results.

Two chips were created for each additive studied, with one serving as the experimental chip and the other as the negative control chip. The experimental chip received 45 µg/mL human IgG in MPBS containing an additional 3 mM ethylene diamine tetraacetic acid and 0.005% Tween-20 ("MPBS-ET") as a target solution. Due to the sensitivity of AIR, 45 µg/mL is considered to be a "high concentration" of target. The use of a high concentration of target served to give rise to a large signal change for the anti-human IgG spots, thereby exaggerating morphological inconsistencies and allowing for easier comparisons of antibody activity. The negative control chip received a solution of MPBS-ET alone, and spot intensity values from this chip acted as background intensities for the experimental chip. After target solutions had incubated, the chips were thoroughly washed with ddH$_2$O and dried under a stream of nitrogen before imaging.

As shown in Table 1 below, the average thickness as measured by spectroscopic ellipsometry is presented for the additive and the anti-human IgG layers formed by incubating the glutaraldehyde chips with a solution containing either only the additives or 500 µg/mL antibody along with different additives. The standard deviations were calculated from the three chips that were measured for each sample.

TABLE 1

Results of Ellipsometry Analysis

| Additive | Additive concentration | Anti-human IgG concentration | Average thickness (Å) | Standard deviation (n = 3) |
|---|---|---|---|---|
| MPBS buffer only | NA | 0 | −0.1 | 0.4 |
| Glycerol | 20% | 0 | 0.1 | 0.3 |
| Triton X 100 | 0.1% | 0 | −1.0 | 0.5 |
| 12-crown-4 | 1% | 0 | −0.2 | 0.2 |
| 18-crown-6 | 1% | 0 | 0.0 | 0.3 |
| Diethyl ether | 1% | 0 | −0.4 | 0.2 |
| DMSO | 1% | 0 | −0.5 | 0.1 |
| Diglyme | 1% | 0 | −0.9 | 0.3 |

TABLE 1-continued

Results of Ellipsometry Analysis

| Additive | Additive concentration | Anti-human IgG concentration | Average thickness (Å) | Standard deviation (n = 3) |
|---|---|---|---|---|
| PEG DME 2000 | 1% | 0 | −0.3 | 0.1 |
| MPBS buffer only | NA | 500 µg/mL | 32.1 | 0.4 |
| Glycerol | 20% | 500 µg/mL | 18.9 | 1.1 |
| Triton X 100 | 0.1% | 500 µg/mL | 16.0 | 0.3 |
| 12-crown-4 | 1% | 500 µg/mL | 35.0 | 0.4 |
| 18-crown-6 | 1% | 500 µg/mL | 29.2 | 0.3 |
| Diethyl ether | 1% | 500 µg/mL | 34.9 | 0.4 |
| DMSO | 1% | 500 µg/mL | 32.3 | 0.8 |
| Diglyme | 1% | 500 µg/mL | 33.4 | 1.0 |
| PEG DME 2000 | 1% | 500 µg/mL | 32.4 | 0.3 |

Spectroscopic ellipsometry provided information about the extent to which the tested additives inhibit/enhance antibody immobilization on glutaraldehyde surfaces. While none of the additives were found to produce a measurable layer of residue on the surface themselves in the absence of the antibody, an expected result given the post-exposure wash with pH 6.0 water, some of them did have a significant effect on the antibody immobilization (Table 1). In particular, it was found that the inclusion of glycerol or Triton X-100 into the spotting buffer greatly inhibited the thickness of the immobilized anti-human IgG layer with respect to buffer alone, showing that these two additives compete with antibody immobilization. On the other hand, 12-crown-4 and diethyl ether helped to slightly increase the thickness of the attached antibody layer. The layer thickness is proportional to the amount of immobilized molecules and in this manner, one of two outcomes may occur: thicker layers accounting for more probe molecules may be available to bind a greater number of target molecules or steric crowding may inhibit binding interactions. This is easily examined using AIR.

For AIR, chips were mounted onto a benchtop reflectometer (Bhattacharjya et al., "Effects of Organic Solvents on Protein Structures: Observation of a Structured Helical Core in Hen Egg-White Lysozyme in Aqueous Dimethylsulfoxide," *Protein Struct. Func. Genet.* 29:492-507 (1997), which is hereby incorporated by reference in its entirety) and images were acquired with Astro IIDC (Aupperle Services and Contracting) using a gain of 1 and at an integration time of 30 ms. The 2 cm×1 cm chips used in this experiment were imaged obliquely at a fixed angle of ~70.5°. The oblique angle of incidence caused the otherwise circular spots to look elliptical in the acquired images. The combination of oblique incidence angle and a relatively large chip size also gives rise to a lack of focal depth over the image. If the array is not in focus, a de-focusing or "pillowing" effect is noticed as an imaging artifact. Therefore, images were also acquired by scanning through five different focal planes along the chip surface to obtain unambiguous reflectance intensities from all spots in the array. Scanning itself has an undesired effect by modulating the magnification of the image. Due to this, compiling a coherent aggregate image requires manipulating the dimensions of raw image. However, since this presents information more accurately describing the morphology and reflectance intensity of each spot, all images used for analysis were a combination of all five focal planes. For comparisons, FIGS. 5A-F show each focal plane independently as well as the resulting combination.

After the images were acquired, the intensity histogram of each spot was obtained using ImageJ (Abramoff et al., "Image Processing with ImageJ," *Biophotonics International* 11:36-42 (2004), which is hereby incorporated by reference in its entirety) and Origin7 (OriginLab). This was fit to a Gaussian, the center of which was taken to be the mean intensity of the spot. The change in intensity for each spot between the control chip and the experimental chip was determined and normalized to any intensity change observed for the negative control anti-fluorescein spots. This reflectance change was normalized to the MPBS standard arraying buffer, and quantified as a "percent active".

FIG. 6A depicts representative spots of each kind from an anti-human IgG array and the area intensity profiles derived from a single spot of anti-human IgG in phosphate buffer alone (FIG. 6B) versus a spot of anti-human IgG in phosphate buffer with 0.1% v/v 12-crown-4 additive (FIG. 6C). The tighter Gaussian profile and the absence of a large number of high intensity pixels make it evident that the presence of the additive creates a more homogenous intensity distribution across the entire area of the spot.

Inhomogeneity in the spot causes deviations from this ideal behavior that are readily observable. For example, bright center regions lead to broadening of the intensity profile resulting from the superposition of a lower-intensity spot domain (the outer portion of the spot) with a higher-intensity domain (the bright center region). Bright outer ("coffee stain") rings have a similar effect. In some cases, fully saturated or high-intensity pixels have been observed. Overall characterization of the spot morphology used this area intensity profile in combination with visual identification of bright center spots (and their area, if present), or outer rings. The AIR results, and the analysis of these features, are presented in Table 2 below.

Most of the additives tested could successfully remove the bright rings usually observed on the periphery of protein spots, but only a few could remove the bright central feature. Triton-X 100 could not be used for the AIR experiments as the hand-arrayed spots containing the detergent coalesced during the course of the experiment. While 20% glycerol was found to have good overall spot morphology, the average reflectance change upon target addition was largely compromised due to a smaller amount of immobilized antibody, consistent with the ellipsometric results. 1% diethyl ether could entirely ablate the bright central feature, and preserve antibody activity during immobilization; however, it could not remove the bright outer rings in the spots. 0.1% v/v 12-crown-4 and 0.1% v/v DMSO had comparable performance, but owing to slightly better antibody activity, 0.1% 12-crown-4 in MPBS was determined to be the best arraying buffer amongst the ones tested on the basis of its ability to remove morphological anomalies, non-competition during antibody immobilization and preservation of the antibody activity on the chip.

TABLE 2

Spot Morphology and Detection Performance of Anti-human IgG Immobilized in the Presence of Various Additives, as Evaluated by AIR

| Additive | Concentration | Outer ring | Average area of central feature[a] (%) | Average reflectance change[b] (%) |
|---|---|---|---|---|
| MPBS | NA | Y | 12.83 | 100 |
| Glycerol | 20% | N | 0.00 | 25.96 |
|  | 2% | Y | 0.00 | 67.31 |
|  | 0.2% | Y | 0.00 | 60.57 |
| 12-crown-4 | 1% | N | 3.81 | 99.32 |
|  | 0.1% | N | 0.00 | 82.02 |
|  | 0.01% | Y | 14.77 | 72.29 |

TABLE 2-continued

Spot Morphology and Detection Performance of
Anti-human IgG Immobilized in the Presence
of Various Additives, as Evaluated by AIR

| Additive | Concentration | Outer ring | Average area of central feature[a] (%) | Average reflectance change[b] (%) |
|---|---|---|---|---|
| 18-crown-6 | 1% | Y | 0.00 | 45.34 |
| | 0.1% | Y | 16.90 | 87.68 |
| | 0.01% | Y | 38.86 | 55.68 |
| Diethyl ether | 1% | Y | 0.00 | 92.12 |
| | 0.1% | N | 19.00 | 78.91 |
| | 0.01% | Y | 5.03 | 89.34 |
| DMSO | 1% | Y | 0.00 | 62.59 |
| | 0.1% | N | 0.00 | 74.55 |
| | 0.01% | N | 0.00 | 79.64 |
| Diglyme | 1% | N | 6.41 | 89.60 |
| | 0.1% | N | 11.06 | 91.34 |
| | 0.01% | N | 3.43 | 98.67 |
| PEG DME | 1% | NA[c] | NA[c] | NA[c] |
| | 0.1% | N | 20.98 | 87.15 |
| | 0.01% | N | 24.77 | 89.2 |

[a]The average central feature area is the percentage of the total spot that is accounted for by the bright center spots.
[b]The average reflectance change was computed from the reflectance change values of each of three spots of a kind on the chip, and corresponds to the spot intensity change after the array was incubated with the human IgG target solution; the changes are normalized to the MPBS standard, and quantified as percent active. Averages have been calculated for three spots.
[c]The 1% PEG-DME spots were not analyzable due to a large amount of scattered intensity observed in the spots.

The above example demonstrates the efficacy of several new non-nucleophilic substances that can be used as additives in protein arrays to improve spot morphology. Importantly, the non-nucleophilic additives do not interfere with protein immobilization and protein activity on the surface. The inert nature of these additives makes them potentially suitable for use with any kind of attachment chemistry. While several of the additives tested had good performance, 0.1% v/v 12-crown-4 has the best observed combination of morphology and antibody activity. Although this study was carried out with large spots (0.5 μL volume, ~0.5 mm diameter), the morphological inhomogeneity issues addressed herein are also common in antibody or protein microarrays (MacBeath et al., "Printing Proteins as Microarrays for High-Throughput Function Determination," *Science* 289:1760-1763 (2000); Deng et al., "Transport at the Air/Water Interface is the Reason for Rings in Protein Microarrays," *J. Am. Chem. Soc.* 128:2768-2769 (2006), which are hereby incorporated by reference in their entirety), and hence the use of these additives should be extended to microarrayed spots. The use of these additives produces a clear, measurable improvement in the performance of AIR protein-detection chips, and it is believed that these results will readily extend to any sensor for which covalent attachment of the probe molecule to a chip surface is required.

Example 3

Figure 7:
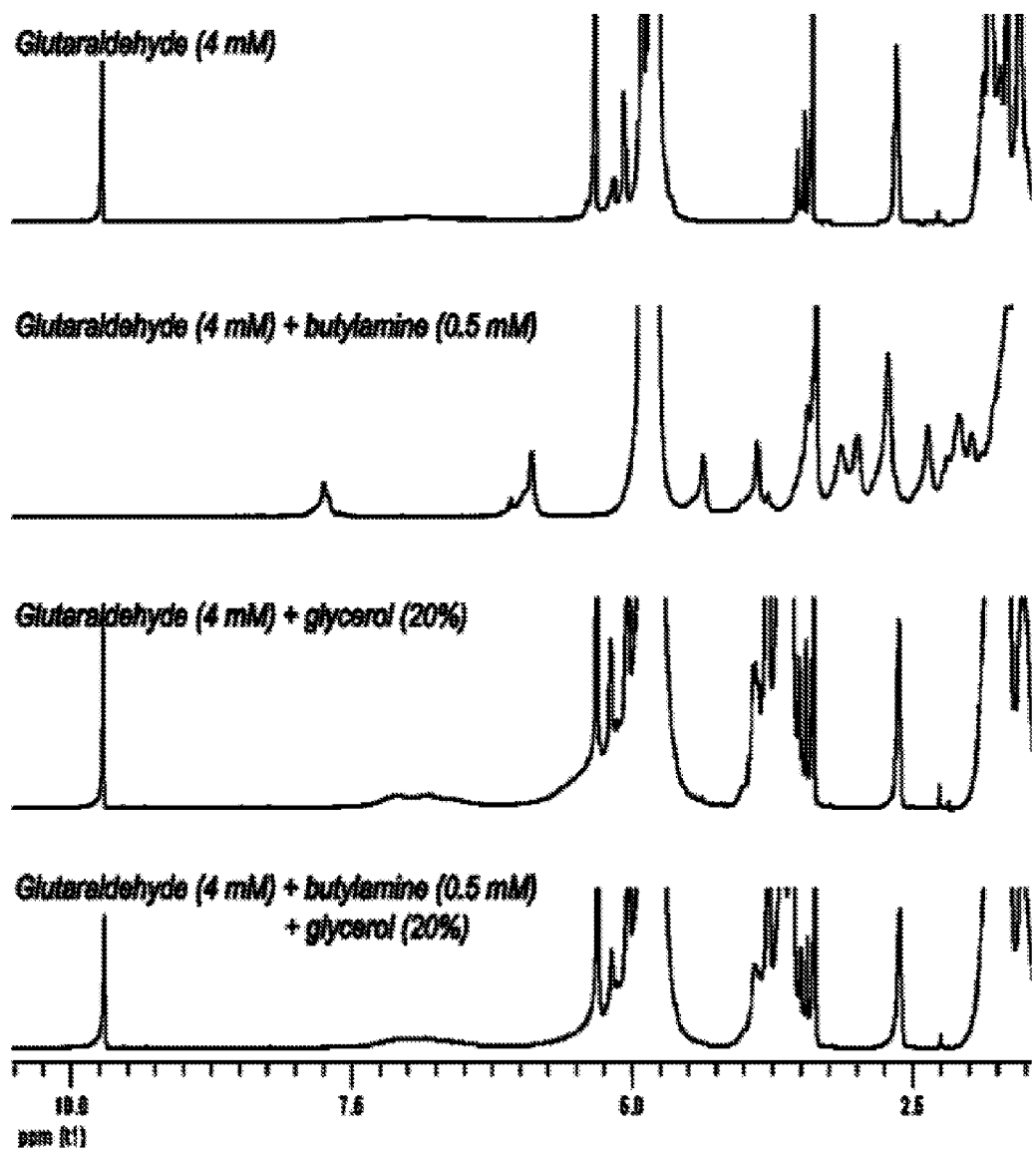
FIG. 7 illustrates a comparison of 1H NMR spectra (500 MHz, Bruker) obtained for glutaraldehyde with butylamine and/or glycerol in MPBS-d, pH 7.2.

Solution NMR Analysis of Glutaraldehyde in the Presence of Butylamine and/or Glycerol Although not a precise analog of the surface reactions discussed in the preceding Examples, a comparison of $^1$H NMR spectra (500 MHz, Bruker) obtained for glutaraldehyde with butylamine and/or glycerol in MPBS-d, pH 7.2 is instructive. In the presence of butylamine, glutaraldehyde forms dihydropyridine and a variety of polymeric products, consistent with prior reports (Lubig et al., "Zum Reaktionsmechanismus von Glutaraldehyde mit Proteinen," *Monatshefte Chem.* 112:1313-1323 (1981), which is hereby incorporated by reference in its entirety). A glutaraldehyde solution containing both butylamine and 20% glycerol, however, shows no evidence of these products. Portions of the relevant spectra are shown in FIG. 7.

All of the features described herein (including any accompanying claims, abstract and drawings), and/or all of the steps of any method or process so disclosed, may be combined with any of the above aspects in any combination, except combinations where at least some of such features and/or steps are mutually exclusive. Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method of coupling a polypeptide reactant to a functionalized surface comprising:
providing a surface comprising a reactive functional group; and
introducing onto the surface, at a plurality of discrete locations, two or more compositions comprising a different polypeptide reactant and a non-nucleophilic additive wherein glycerol is not present in the two or more compositions, said introducing being effective to allow for covalent binding of the polypeptide reactant to the surface via the reactive functional group in the absence of glycerol,
wherein the non-nucleophilic additive comprises a structure according to formula (I) present in an amount of 0.001 to 3 percent v/v:

$$R^1-O-[(CH_2)_mO]_n-R^2 \quad (I)$$

where
n is an integer from 0 to about 250,
m is an integer from 1 to about 3, and
$R^1$ and $R^2$ are independently selected from the group of a C1 to C3 alkyl, or $R^1$ and $R^2$ together form a C1 to C3 alkyl, in which case the compound of formula (I) has a cyclic structure, or
wherein the non-nucleophilic additive is dimethylsulfoxide (DMSO) present in an amount of 0.01 to 1 percent v/v.

2. The method according to claim 1, wherein the non-nucleophilic additive comprises a structure according to formula (I).

3. The method according to claim 2, wherein the non-nucleophilic additive according to formula (I) has a molecular weight that is about 5000 Da or less.

4. The method according to claim 2, wherein the non-nucleophilic additive comprises a cyclic structure, where $R^1$ and $R^2$ together form a C1 to C3 alkyl.

5. The method according to claim 4, wherein the non-nucleophilic additive is a crown ether.

6. The method according to claim 2, wherein the non-nucleophilic additive comprise a non-cyclic structure, where $R^1$ and $R^2$ are independently selected from the group of a C1 to C3 alkyl.

7. The method according to claim 2, wherein the non-nucleophilic additive according to formula (I) is present in an amount of about 0.01 to about 1 percent v/v.

8. The method according to claim 1, wherein the non-nucleophilic additive is dimethylsulfoxide (DMSO).

9. The method according to claim 1, wherein the non-nucleophilic additive facilitates dispersion of the polypeptide reactant within the composition but does not participate in covalent bond formation.

10. The method according to claim 1, wherein the reactive functional group is an aldehyde group, an activated ester, an isothiocyanate, an azide, an alkyne, a silyl halide, or combinations thereof.

11. The method according to claim 10, wherein the polypeptide reactant comprises an amine, a carboxylic acid, a thiol, an aldehyde, or a primary alcohol.

12. The method according to claim 10, wherein the polypeptide reactant comprises an amine group.

13. The method according to claim 1, further comprising combining the additive into a solution comprising the polypeptide reactant, thereby forming the composition, immediately preceding said introducing.

14. The method according to claim 1, further comprising washing the compositions from the plurality of discrete locations.

15. The method according to claim 1, wherein the non-nucleophilic additive for each of the two or more compositions is the same.

16. The method according to claim 1, wherein the non-nucleophilic additive for the two or more compositions is different.

17. The method according to claim 1, wherein each of the discrete locations has a substantially homogeneous distribution of the polypeptide reactant across said discrete location.

18. The method according to claim 1, wherein each of the discrete locations exhibits, upon imaging, a spot morphology that exhibits less than about 20 percent pixel variation across the discrete location.

19. A method of coupling a polypeptide reactant to a functionalized surface comprising:

providing a surface comprising a reactive functional group; and introducing onto the surface, at a plurality of discrete locations, two or more aqueous compositions comprising a different polypeptide reactant and a non-nucleophilic additive wherein glycerol is not present in the two or more aqueous compositions, said introducing being effective to allow for covalent binding of the polypeptide reactant to the surface via the reactive functional group in the absence of glycerol, wherein the non-nucleophilic additive does not participate in covalent bond formation, and wherein the non-nucleophilic additive comprises a structure according to formula (I) present in an amount of 0.001 to 3 percent v/v:

$$R^1-O-[(CH_2)_mO]_n-R^2 \qquad (I)$$

where n is an integer from 0 to about 250, m is an integer from 1 to about 3, and $R^1$ and $R^2$ are independently selected from the group of a C1 to C3 alkyl, or $R^1$ and $R^2$ together form a C1 to C3 alkyl, in which case the compound of formula (I) has a cyclic structure, or wherein the non-nucleophilic additive is dimethylsulfoxide (DMSO) present in an amount of 0.01 to 1 percent v/v.

20. The method according to claim 19, wherein each of the discrete locations has a substantially homogeneous distribution of the polypeptide reactant across said discrete location.

21. The method according to claim 19, wherein each of the discrete locations exhibits, upon imaging, a spot morphology that exhibits less than about 20 percent pixel variation across the discrete location.

* * * * *